(12) United States Patent  
Degroot et al.

(10) Patent No.: US 8,478,399 B2
(45) Date of Patent: Jul. 2, 2013

(54) METHOD AND APPARATUS FOR CONTROLLING ARRHYTHMIA DETECTION AND TREATMENT BASED ON PATIENT POSTURE

(76) Inventors: Paul J. Degroot, Brooklyn Park, MN (US); Karel F. A. A. Smits, Munstergeleen (NL); William J. Flickinger, Lino Lakes, MN (US)

( * ) Notice: Subject to any disclaimer, the term of this patent is extended or adjusted under 35 U.S.C. 154(b) by 1459 days.

(21) Appl. No.: 11/343,346

(22) Filed: Jan. 31, 2006

(65) Prior Publication Data

US 2007/0179539 A1    Aug. 2, 2007

(51) Int. Cl.
*A61N 1/00* (2006.01)
(52) U.S. Cl.
USPC ..................................... 607/4; 607/5; 607/6
(58) Field of Classification Search
USPC ............................................ 607/4, 5, 6
See application file for complete search history.

(56) References Cited

U.S. PATENT DOCUMENTS

| | | | |
|---|---|---|---|
| 4,180,078 A | 12/1979 | Anderson | |
| 4,374,382 A | 2/1983 | Markowitz | |
| 4,548,209 A | 10/1985 | Wielders et al. | |
| 4,556,063 A | 12/1985 | Thompson et al. | |
| 4,567,892 A | 2/1986 | Plicchi | |
| 5,127,404 A | 7/1992 | Wyborny et al. | |
| 5,163,427 A | 11/1992 | Keimel | |
| 5,176,137 A | 1/1993 | Erickson | |
| 5,188,105 A | 2/1993 | Keimel | |
| 5,193,535 A | 3/1993 | Bardy et al. | |
| 5,318,591 A * | 6/1994 | Causey et al. ................. | 607/5 |
| 5,354,316 A | 10/1994 | Keimel | |
| 5,464,434 A | 11/1995 | Alt | |
| 5,470,345 A | 11/1995 | Hassler et al. | |
| 5,501,701 A | 3/1996 | Markowitz et al. | |
| 5,545,186 A | 8/1996 | Olson et al. | |
| 5,593,431 A | 1/1997 | Sheldon | |
| 5,683,432 A | 11/1997 | Goedeke et al. | |
| 5,855,593 A | 1/1999 | Olson et al. | |
| 5,865,760 A | 2/1999 | Lidman et al. | |
| 6,044,297 A | 3/2000 | Sheldon et al. | |
| 6,236,882 B1 | 5/2001 | Lee et al. | |
| 6,482,154 B1 | 11/2002 | Haubrich et al. | |
| 6,512,940 B1 | 1/2003 | Brabec et al. | |
| 6,522,915 B1 | 2/2003 | Ceballos et al. | |
| 6,622,046 B2 | 9/2003 | Fraley et al. | |
| 6,892,094 B2 | 5/2005 | Ousdigian et al. | |
| 7,181,281 B1 * | 2/2007 | Kroll ............................. | 607/14 |
| 2002/0188215 A1 * | 12/2002 | Ferek-Petric ................. | 600/518 |
| 2003/0204209 A1 | 10/2003 | Burnes et al. | |
| 2004/0106962 A1 | 6/2004 | Mai et al. | |

* cited by examiner

*Primary Examiner* — George Manuel
*Assistant Examiner* — William Levicky
(74) *Attorney, Agent, or Firm* — Michael C. Soldner

(57) ABSTRACT

An implantable medical device and method are provided for determining if a patient is in a substantially horizontal position and delaying a programmed cardioversion/defibrillation shock therapy in response to determining the patient is in a substantially horizontal position. In various embodiments, the shock therapy may be delayed by adjusting tachycardia detection criteria or scheduling the shock therapy after a maximum tachycardia episode duration.

21 Claims, 4 Drawing Sheets

METHOD AND APPARATUS FOR CONTROLLING ARRHYTHMIA DETECTION AND TREATMENT BASED ON PATIENT POSTURE

TECHNICAL FIELD

The invention relates generally to medical devices, and more particularly, to a method and apparatus for detecting and treating arrhythmias in a medical device based on patient posture.

BACKGROUND

Implantable medical devices are available for preventing or treating cardiac arrhythmias by delivering anti-tachycardia pacing therapies and electrical shock therapies for cardioverting or defibrillating the heart. Such a device, commonly known as an implantable cardioverter defibrillator or "ICD", senses a patient's heart rhythm and classifies the rhythm according to a number of rate zones in order to detect episodes of tachycardia or fibrillation. Rate zone classifications typically include normal sinus rhythm, tachycardia, and fibrillation. Both atrial and ventricular arrhythmias may be detected and treated.

Upon detecting an abnormal rhythm, the ICD delivers an appropriate therapy. Cardiac pacing is delivered in response to the absence of sensed intrinsic depolarizations, referred to as P-waves in the atrium and R-waves in the ventricle, upon the expiration of defined escape intervals. Ventricular fibrillation (VF) is a form of tachycardia that is a serious life-threatening condition and is normally treated by immediately delivering high-energy shock therapy. Termination of VF is normally referred to as "defibrillation."

Other forms of ventricular tachycardia (VT) may be debilitating, but do not necessarily pose an immediately life-threatening situation. Cardiac output tends to be compromised due to the disorganized contraction of the myocardial tissue resulting in a patient feeling weak, dizzy or even fainting. Ventricular tachycardia may, however, degenerate into a more unstable heart rhythm, leading to ventricular fibrillation. Both VF and VT can result in syncope. Syncope, or fainting, can cause serious injury to the patient, particularly, for example, when the patient is standing or driving a car. A detected VT is generally responded to quickly with either anti-tachycardia pacing therapies or cardioversion shocks. Because VT can often be terminated by anti-tachycardia pacing therapies, these therapies are generally delivered first, because they are less painful to the patient and are followed by high-energy shock therapy only when necessary. Termination of a tachycardia by a shock therapy is commonly referred to as "cardioversion."

In response to tachycardia detection, a number of tiered therapies may be delivered beginning with anti-tachycardia pacing therapies and escalating to more aggressive shock therapies until the tachycardia is terminated. In modern ICDs, the physician programs the particular therapies into the device ahead of time, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher energy shock pulse may be selected. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. For an overview of tachycardia detection and treatment therapies reference is made to U.S. Pat. No. 5,545,186 issued to Olson et al., hereby incorporated herein by reference in its entirety. Accurate tachycardia detection and discrimination are important in selecting the appropriate therapy and avoiding the delivery of unnecessary or unsuccessful cardioversion/defibrillation (CV/DF) shocks, which are painful to the patient. Avoiding patient injury due to syncope is also desirable.

DETAILED DESCRIPTION

In the following description, references are made to illustrative embodiments for carrying out the invention. It is understood that other embodiments may be utilized without departing from the scope of the invention. The invention is directed toward providing an implantable device, used for detecting and treating cardiac arrhythmias, that uses a determination of patient posture in detecting an arrhythmia and/or in scheduling a shock therapy. Arrhythmia detection and treatment algorithms that include a determination of patient posture may be implemented in any ICD equipped with a posture sensor, including ICDs coupled to transvenous leads extending to intracardiac implant sites and subcutaneous ICDs, referred to herein as "SubQ ICDs", which are coupled to a subcutaneous lead or to no leads at all. For a description of an ICD used in conjunction with transvenous leads, reference is made to the above-incorporated '186 Olson patent.

Figure 1:
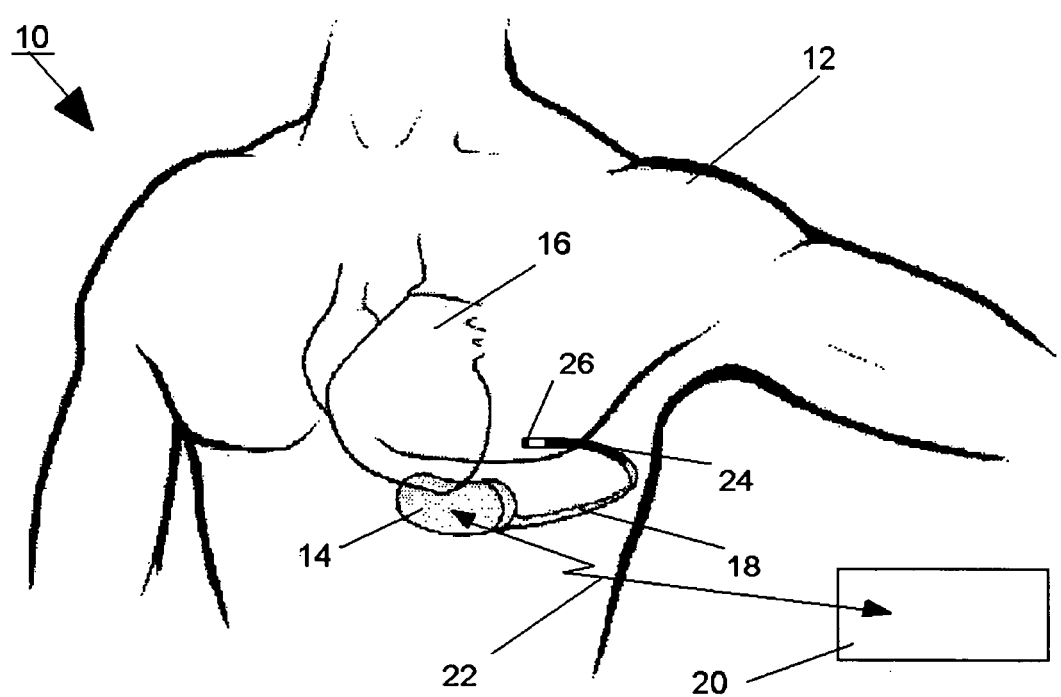
FIG. 1 shows a subcutaneous ICD implanted in a patient.

FIG. 1 shows SubQ ICD 14 implanted in patient 12. The SubQ ICD 14 is subcutaneously implanted outside the ribcage of patient 12, anterior to the cardiac notch. A subcutaneous sensing and CV/DF therapy delivery lead 18 in electrical communication with SubQ ICD 14 is tunneled subcutaneously into a location adjacent to a portion of a latissimus dorsi muscle of patient 12. Specifically, lead 18 is tunneled subcutaneously from the median implant pocket of SubQ ICD 14 laterally and posteriorly to the patient's back to a location opposite the heart such that the heart 16 is generally disposed between the SubQ ICD 14 and the distal electrode coil 24 and distal sensing electrode 26 of lead 18.

An external programmer 20 is shown in telemetric communication with SubQ ICD 14 by RF communication link 22. Communication link 22 may be any appropriate RF link such as Bluetooth, WiFi, MICS, or as described in U.S. Pat. No. 5,683,432 "Adaptive Performance-Optimizing Communication System for Communicating with an Implantable Medical Device" to Goedeke, et al., and incorporated herein by reference in its entirety.

Figure 2:
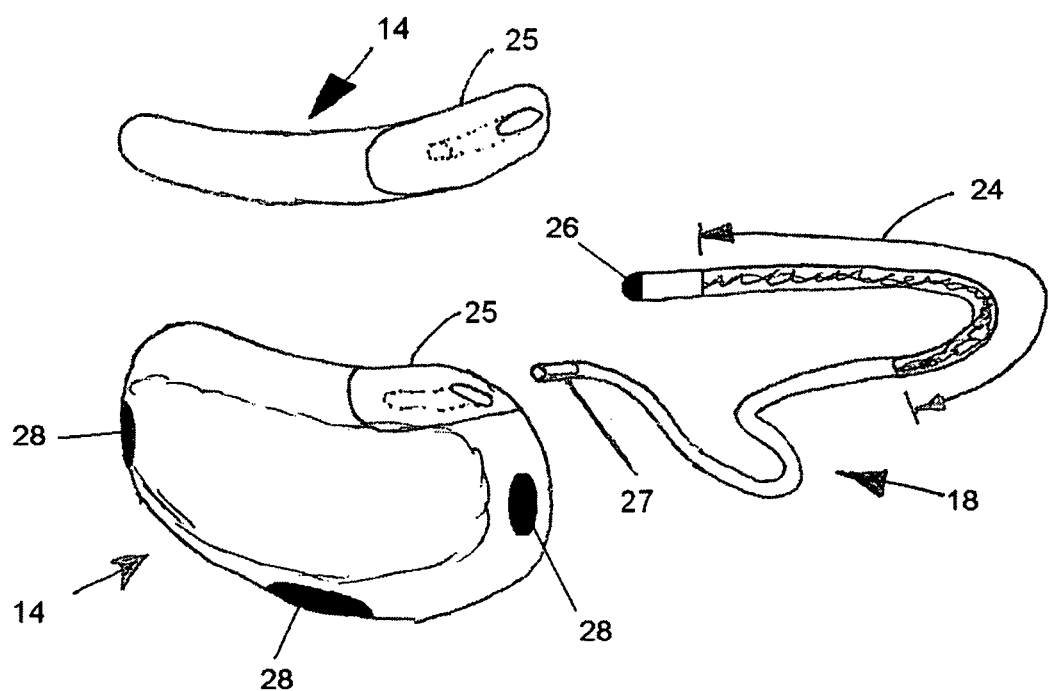
FIG. 2 is a frontal and plan view of the subcutaneous ICD shown in FIG. 1.

FIG. 2 is a frontal and plan view of SubQ ICD 14. SubQ ICD 14 is generally ovoid and includes a substantially kidney-shaped profile formed by a housing with a connector 25 for attaching subcutaneous sensing and CV/DF therapy delivery lead 18. The housing of SubQ ICD 14 may be constructed of stainless steel, titanium or ceramic as generally described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al, both incorporated herein by reference in their entireties. Electronics circuitry enclosed within the housing of SubQ ICD 14 may be incorporated on a polyamide flex circuit, printed circuit board (PCB) or ceramic substrate with integrated circuits packaged in leadless chip carriers and/or chip scale packaging (CSP). The plan view shows the ovoid construction that promotes ease of subcutaneous implant. This structure is ergonomically adapted to minimize patient discomfort during normal body movement and flexing of the thoracic musculature.

Subcutaneous lead 18 includes a distal defibrillation coil electrode 24, a distal sensing electrode 26, an insulated flexible lead body and a proximal connector pin 27 for connection to SubQ ICD housing via connector 25. Distal sensing electrode 26 is sized appropriately to match the sensing impedance of the housing-based subcutaneous electrode arrays (SEA) 28 (three electrodes included in SEA 28 are shown in FIG. 2).

SEA assemblies are welded into place on the flattened periphery of the SubQ ICD housing. In the embodiment shown, the complete periphery of the SubQ ICD may be manufactured to have a slightly flattened perspective with rounded edges to accommodate the placement of SEA assemblies. The SEA assemblies are welded to SubQ ICD housing (to preserve hermeticity) and are electrically connected to electronic circuitry inside the ICD housing. SEA 28 may be constructed of flat plates, or alternatively, spiral electrodes as described in U.S. Pat. No. 6,512,940 "Subcutaneous Spiral Electrode for Sensing Electrical Signals of the Heart" to Brabec, et al and mounted in a non-conductive surround shroud as described in U.S. Pat. No. 6,522,915 "Surround Shroud Connector and Electrode Housings for a Subcutaneous Electrode Array and Leadless ECGs" to Ceballos, et al and U.S. Pat. No. 6,622,046 "Subcutaneous Sensing Feedthrough/Electrode Assembly" to Fraley, et al, all of which patents are hereby incorporated herein by reference in their entireties. The electrodes included in SEA 28 are positioned to form orthogonal signal vectors.

The electronic circuitry employed in SubQ ICD 14 can take any form that detects a tachyarrhythmia from the sensed ECG signal and provides CV/DF shocks. Other pacing therapy capabilities may be provided including anti-tachycardia pacing (ATP) therapies as well as post-shock pacing sometimes needed while the heart recovers from a CV/DF shock. A simplified block diagram of ICD circuitry adapted to function employing subcutaneous CV/DF electrodes as well as subcutaneous ECG sensing and pacing electrodes is set forth in FIG. 3. It will be understood that the simplified block diagram does not show all of the conventional components and circuitry that may be included in ICDs including digital clocks and clock lines, low voltage power supply and supply lines for powering the circuits and providing pacing pulses or telemetry circuits for telemetry transmissions between the SubQ ICD 14 and external programmer 20.

Figure 3:
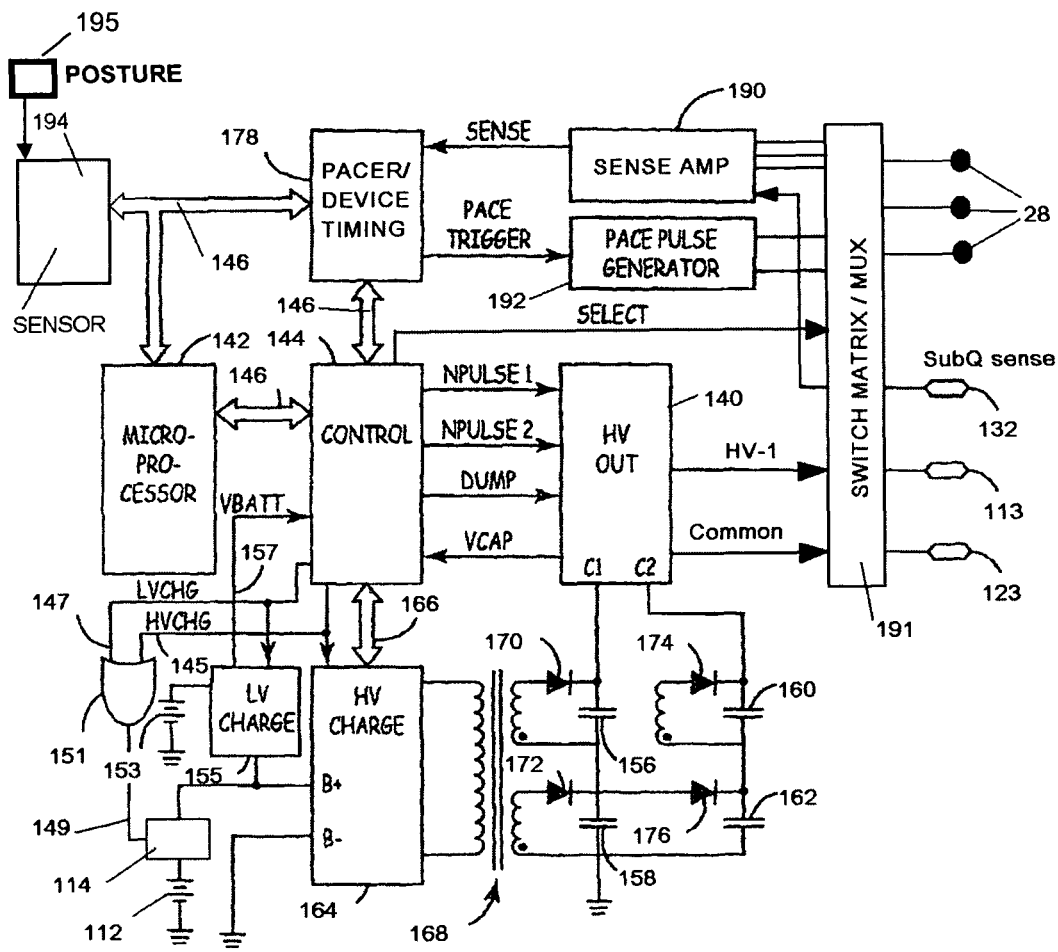
FIG. 3 depicts electronic circuit components enclosed in hermetically sealed housing of an ICD.

FIG. 3 depicts electronic circuit components enclosed in hermetically sealed housing of SubQ ICD 14. The low voltage battery 153 is coupled to a power supply that supplies power to the SubQ ICD 14 circuitry and the pacing output capacitors to supply pacing energy. The low voltage battery may include, for example, one or two conventional LiCFx, LiMnO2 or Lil2 cells. The high voltage battery 112 may include, for example, one or two conventional LiSVO or LiMnO2 cells.

SubQ ICD functions are controlled by means of software, firmware and hardware that cooperatively monitor the ECG signals, determine when a CV/DF shock or anti-tachyarrhythmia pacing (ATP) is necessary, and deliver prescribed CV/DF shock and ATP therapies according to programmed tiered-therapy menus. As will be described herein, a programmed CV/DF shock may be delayed based on feedback received from a postures sensor. The block diagram of FIG. 3 incorporates circuitry set forth in commonly-assigned U.S. Pat. No. 5,163,427 "Apparatus for Delivering Single and Multiple Cardioversion and Defibrillation Pulses" to Keimel; and U.S. Pat. No. 5,188,105 "Apparatus and Method for Treating a Tachyarrhythmia" to Keimel for selectively delivering single phase, simultaneous biphasic and sequential biphasic CV/DF shocks. A CV/DF shock is delivered using an ICD housing electrode coupled to the COMMON output 123 of high voltage output circuit 140 and the CV/DF electrode 24 disposed posterially and subcutaneously and coupled to the HVI output 113 of the high voltage output circuit 140.

The CV shock energy and capacitor charge voltages are generally intermediate to those supplied by ICDs having at least one CV electrode in contact with the heart and most automatic external defibrillators (AEDs) having CV electrodes in contact with the skin. The typical maximum voltage necessary for successful cardioversion using biphasic waveforms delivered by ICDs coupled to intracardiac electrodes is approximately 750 Volts with an associated maximum energy of approximately 40 Joules. The typical maximum voltage necessary for successful cardioversion using AEDs is approximately 2000-5000 Volts with an associated maximum energy of approximately 200-360 Joules depending upon the model and waveform used. A SubQ ICD uses maximum voltages in the range of about 700 to about 3150 Volts and is associated with energies of about 25 Joules to about 210 Joules. The total high voltage capacitance could range from about 50 to about 300 microfarads. Such CV/DF shocks are typically programmed for delivery only when a malignant tachyarrhythmia, e.g., ventricular fibrillation, is detected through processing of the cardiac ECG signals.

Sense amplifier 190 in conjunction with pacer/device timing circuit 178 processes the far field ECG sense signal that is received across a particular ECG sense vector defined by a selected pair of the subcutaneous electrodes 28. The selection of the sensing electrode pair is made through the switch matrix/MUX 191 in a manner to provide the most reliable sensing of the ECG signal of interest. The far field ECG signals are passed through the switch matrix/MUX 191 to the input of the sense amplifier 190, which, in conjunction with pacer/device timing circuit 178, evaluates the sensed ECG signal. Bradycardia, or asystole, is typically determined by the expiration of an escape interval timer within the pacer timing circuit 178 and/or the control circuit 144. Pace trigger signals are applied to the pacing pulse generator 192 to trigger pacing pulse generation upon expiration of an escape interval timer. Bradycardia pacing is often temporarily provided to maintain cardiac output after delivery of a CV/DF shock that may cause the heart to slowly beat as it recovers back to normal function. Accurate subcutaneous sensing of far field ECG signals in the presence of noise may be improved by the use of appropriate denial and extensible accommodation periods as described in U.S. Pat. No. 6,236,882 "Noise Rejection for Monitoring ECGs" to Lee, et al and incorporated herein by reference in its entirety.

Detection of a malignant tachycardia is determined in the control circuit 144 as a function of the intervals between R-wave sense event signals that are output from the pacer/device timing 178 and sense amplifier circuit 190 to the timing and control circuit 144. Interval based signal analysis as well as ECG morphology analysis and processing of other sensor signals may be incorporated in arrhythmia detection schemes used by SubQ ICD 14. As will be described in greater detail herein, a posture sensor 195 is included in the SubQ ICD system for providing a signal responsive to patient posture to sensor processing block 194. Posture sensor 195 may be incorporated on or in SubQ ICD housing or carried by the subcutaneous lead 18 extending from SubQ ICD 14 (as shown in FIG. 1). Posture sensor 195 may be embodied as generally described in U.S. Pat. No. 5,593,431 "Medical Device Employing Multiple DC Accelerometers for Patient Activity and Posture Sensing and Method" to Sheldon, or in U.S. Pat. No. 6,044,297 "Posture and Device orientation and Calibration for Implantable Medical Devices" to Sheldon, et al., both patents hereby incorporated herein by reference in their entirety.

Sensor processing block 194 provides posture sensor data to microprocessor 142 and/or control circuit 144 via data bus 146. Posture sensor 195 is implemented to discriminate a substantially horizontal position from a substantially upright position. Typically, SubQ ICD 14 monitors signals generated by one or more accelerometers to detect the patient's posture. A substantially horizontal position may be a prone or supine position that can be detected when the posture sensor is implemented in SubQ ICD 14 implanted in the frontal plane. Specifically, sensor processing block 194 may compare the DC signal component of an accelerometer implanted in a stable position relative to the patient's anatomy and generally aligned with an axis of the patient's body. Two or three orthogonally-arranged accelerometers may be used in some embodiments for identifying postures by comparing the DC signal components to one or more thresholds. For example, posture sensor 195 can be implemented and calibrated to provide detection of lateral and upright positions. For example, when posture sensor 195 is implemented as a three dimensional gravitational sensor, the sensor can be calibrated at the time of implant or during patient follow-up for known patient positions.

Supplemental sensors such as hemodynamic sensors, tissue color, tissue oxygenation, respiration, patient activity and the like may be used to contribute to the decision to apply or withhold a defibrillation therapy. Reference is made, for example, to U.S. Pat. No. 5,464,434 "Medical Interventional Device Responsive to Sudden Hemodynamic Change" to Alt and incorporated herein by reference in its entirety. Patient respiration may be determined by the apparatus and method as described in U.S. Pat. No. 4,567,892 "Implantable Cardiac Pacemaker" to Plicchi, et al and incorporated herein by reference in its entirety. Patient tissue oxygenation or tissue color may be determined by the sensor apparatus and method as generally described in U.S. Pat. No. 5,176,137 to Erickson, et al and incorporated herein by reference in its entirety. The oxygen sensor of the '137 patent may be located in the SubQ ICD pocket or, alternatively, located on the lead 18 to enable sensing of contacting or near-contacting tissue oxygenation or color. A hemodynamic sensor or heart rate sensor may be used in the detection of syncope, for example as generally described in U.S. Pat. No. 5,501,701 issued to Markowitz et al., hereby incorporated herein by reference in its entirety.

Certain steps in the performance of arrhythmia detection algorithms are cooperatively performed in microprocessor 142, including RAM and ROM, associated circuitry, and stored detection criteria that may be programmed into RAM via a telemetry interface. Data and commands are exchanged between microprocessor 142 and timing and control circuit 144, pacer/device timing 178, and high voltage output circuit 140 via a bidirectional data/control bus 146. The pacer/device timing circuit 178 and the control circuit 144 are clocked at a slow clock rate. Microprocessor 142 operates as an interrupt controlled device and is normally in a sleep state. Microprocessor 142 is awakened and operated by a fast clock in response to interrupt signals generated by designated ECG sense events, such as R-waves, upon receipt of a downlink telemetry programming instruction, or upon delivery of cardiac pacing pulses. Microprocessor 142 performs any necessary mathematical calculations, including tachycardia and fibrillation detection procedures, and updates time intervals monitored and controlled by the timers in pacer/device timing circuitry 178 upon receiving an interrupt signal.

Examples of algorithms and functions of the microprocessor 142 and control circuit 144 employed and performed in detection of tachyarrhythmias are set forth, for example, in commonly-assigned U.S. Pat. No. 5,354,316 "Method and Apparatus for Detection and Treatment of Tachycardia and Fibrillation" to Keimel; U.S. Pat. No. 5,545,186 "Prioritized Rule Based Method and Apparatus for Diagnosis and Treatment of Arrhythmias" to Olson, et al; U.S. Pat. No. 5,855,593 "Prioritized Rule Based Method and Apparatus for Diagnosis and Treatment of Arrhythmias" to Olson, et al; and U.S. Pat. No. 5,193,535 "Method and Apparatus for Discrimination of Ventricular Tachycardia from Ventricular Fibrillation and Treatment Thereof" to Bardy, et al, (all incorporated herein by reference in their entireties). Particular algorithms for detection of ventricular fibrillation and malignant ventricular tachycardias can be selected from among the comprehensive algorithms for distinguishing atrial and ventricular tachyarrhythmias from one another and from high rate sinus rhythms as set forth in the '316, '186, '593 and '593 patents.

The detection algorithms are highly sensitive and specific for the presence or absence of life threatening ventricular arrhythmias, e.g., ventricular tachycardia (VT) and ventricular fibrillation (VF). Operational circuitry may also be configured to detect the presence of atrial fibrillation (A FIB). For example, A FIB detection can be provided via R-R Cycle length instability detection algorithms. Once A-FIB has been detected, the operational circuitry may schedule a QRS-synchronized, atrial CV/DF shock using the similar shock energy and wave shapes used for ventricular CV/DF.

Operating modes and parameters of the tachycardia detection algorithms are programmable and may be particularly aimed at detecting VF and high rate VT (>180 bpm), which can be life threatening. SubQ ICD 14 includes automatic detection and therapy of the most malignant rhythm disorders. As part of the detection algorithm's applicability to children, the upper rate range is programmable upward for use in children, known to have rapid supraventricular tachycardias and more rapid VF.

Event intervals (R-R intervals) are commonly used for detecting ventricular tachycardias. Additional information obtained from multiple cardiac signals, R-wave morphology, slew rate, other event intervals (P-R intervals) or other sensor signal information may be used in detecting, confirming or discriminating a tachycardia. In one detection scheme, programmable detection interval ranges designate the range of sensed event intervals indicative of a tachycardia and may be defined separately for detecting slow tachycardia, fast tachycardia and fibrillation. Sensed event intervals falling into defined detection interval ranges are counted to provide a count of tachycardia intervals. A programmable number of intervals to detect (NID) defines the number of tachycardia intervals occurring consecutively or out of a given number of preceding event intervals that are required to detect tachycardia. A separately programmed NID may be defined for detecting slow and fast tachycardia and fibrillation. In addition to the interval ranges and NID criteria, rapid onset criterion and rate stability criterion may also be defined for use in tachycardia detection schemes. Furthermore, a combined count of tachycardia and fibrillation intervals may be compared to a combined count threshold and, according to predefined criteria, used in detecting fibrillation or slow or fast tachycardia.

Control circuit 144 controls the delivery of a programmed CV/DF shock in response to a posture signal received from the posture sensor 195. Sensor processing block 194 provides a posture signal from posture sensor 195 to microprocessor 142 and/or control circuit 144 corresponding to either a substantially horizontal position, such as a prone, supine or lateral position, or a substantially upright position, such as a standing or sitting position. Control circuit 144 responds to a substantially horizontal position signal received on data bus 146 by delaying a programmed shock therapy.

In one embodiment of the invention, the tachycardia/fibrillation detection criteria, such as the NID, may be adjusted based on feedback from posture sensor 195. When microprocessor 142 determines that the patient is in a substantially horizontal position, the detection criteria may be adjusted in a way that effectively increases the time required to detect a tachycardia, thereby delaying a shock therapy that is programmed to respond to the detected tachycardia. For example, the patient posture may be monitored continuously with the detection criteria set according to the determined patient posture. If the patient is determined to be in a substantially horizontal position, the tachycardia and/or fibrillation NID may be set to a higher number, allowing SubQ ICD 14 more time to accurately detect the heart rhythm, effectively delaying a programmed shock therapy. If the patient is determined to be in a substantially upright position (e.g., sitting or standing), more aggressive detection criteria are used, such as a lower NID, to allow quicker detection of a tachycardia/fibrillation and subsequently a quicker therapy response.

In another embodiment, a preliminary tachycardia detection is made based on a programmed set of detection criteria. Upon making the preliminary detection, the microprocessor 142 and/or control circuit 144 determines the patient posture using posture sensor 195. If the posture is determined to be substantially horizontal, microprocessor 142 adjusts the detection criteria, such as the NID, to allow more time to confirm the preliminary detection and thereby effectively delays a shock therapy that is programmed to respond to the tachycardia detection. Alternatively, microprocessor 142 and/or control circuit 144 may delay a programmed shock therapy in response to a preliminary tachycardia detection and determination of a substantially horizontal position in order to execute additional tachycardia discrimination algorithms.

When a shock therapy is needed in response to a tachycardia detection, high voltage capacitors 156, 158, 160, and 162 are charged to a pre-programmed voltage level by a high-voltage charging circuit 164. It is generally considered inefficient to maintain a constant charge on the high voltage output capacitors 156, 158, 160, 162. Instead, charging is initiated when control circuit 144 issues a high voltage charge command HVCHG delivered on line 145 to high voltage charge circuit 164 and charging is controlled by means of bidirectional control/data bus 166 and a feedback signal VCAP from the HV output circuit 140. High voltage output capacitors 156, 158, 160 and 162 may be flat aluminum electrolytic or wet tantalum type capacitors. Charging of high voltage capacitors 156, 158, 160, and 162 may be delayed in response to a determination of a substantially horizontal patient position. Alternatively, capacitor charging may be initiated immediately upon a preliminary tachycardia detection such that the high voltage capacitors 156, 158, 160 and 162 are charging during a delay in response to detection of a substantially horizontal position, and during which adjusted tachycardia detection criteria may be applied and/or additional discrimination algorithms may be executed.

The negative terminal of high voltage battery 112 is directly coupled to system ground. Switch circuit 114 is normally open so that the positive terminal of high voltage battery 112 is disconnected from the positive power input of the high voltage charge circuit 164. The high voltage charge command HVCHG is also conducted via conductor 149 to the control input of switch circuit 114, and switch circuit 114 closes in response to connect positive high voltage battery voltage EXT B+ to the positive power input of high voltage charge circuit 164. Switch circuit 114 may be, for example, a field effect transistor (FET) with its source-to-drain path interrupting the EXT B+ conductor 118 and its gate receiving the HVCHG signal on conductor 145. High voltage charge circuit 164 is thereby rendered ready to begin charging the high voltage output capacitors 156, 158, 160, and 162 with charging current from high voltage battery 112.

High voltage output capacitors 156, 158, 160, and 162 may be charged to very high voltages, e.g., 700-3150V, to be discharged through the body and heart between the electrode pair of subcutaneous CV/DF electrodes 113 and 123. High voltage capacitors 156, 158, 160 and 162 are charged by high voltage charge circuit 164 and a high frequency, high-voltage transformer 168, for example, as described in detail in commonly-assigned U.S. Pat. No. 4,548,209 "Energy Converter for Implantable Cardioverter" to Wielders, et al. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP feedback signal indicative of the voltage to the control circuit 144. Control circuit 144 terminates the high voltage charge command HVCHG when the VCAP signal matches the programmed capacitor output voltage, i.e., the CV/DF peak shock voltage.

In another embodiment of the invention, a programmed shock therapy is delayed in response to determining a substantially horizontal position by delaying the charging of high voltage capacitors 156, 158, 160 and 162 until a predetermined episode duration. Alternatively, control circuit 144 triggers the immediate charging of high voltage capacitors 156, 158, 160 and 162 then delays the scheduled delivery of the high voltage shock therapy. The shock delay may be set to a predetermined episode duration or a predetermined time interval after the capacitor charge time. In some embodiments, patient position may continue to be monitored during a shock delay such that the shock delay may be terminated prematurely in response to a detected change in patient position from a substantially horizontal to a substantially upright position. During the shock delay, anti-tachycardia pacing therapies may be delivered, contemporaneously with or prior to capacitor charging. Anti-tachycardia pacing therapies may include, burst pacing, ramp pacing, or ramp-plus pacing. Anti-tachycardia pacing therapies are generally described in the above incorporated Olson patents.

Upon termination of a shock therapy delay, or when a substantially upright position is detected, control circuit 144 controls the delivery of the scheduled shock therapy. Control circuit 144 develops first and second control signals NPULSE 1 and NPULSE 2, respectively, that are applied to the high voltage output circuit 140 for triggering the delivery of cardioverting or defibrillating shocks. In particular, the NPULSE 1 signal triggers discharge of the first capacitor bank, comprising capacitors 156 and 158. The NPULSE 2 signal triggers discharge of the first capacitor bank and a second capacitor bank, comprising capacitors 160 and 162. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 144 serves to control operation of the high voltage output stage 140, which delivers high energy CV/DF shocks between the pair of the CV/DF electrodes 113 and 123 coupled to the HV-1 and COMMON output as shown in FIG. 3.

The high HVCHG signal causes the high voltage battery 112 to be connected through the switch circuit 114 with the high voltage charge circuit 164 and the charging of output capacitors 156, 158, 160, and 162 to commence. Charging continues until the programmed charge voltage is reflected by the VCAP signal, at which point control and timing circuit 144 sets the HVCHG signal low terminating charging and opening switch circuit 114. Typically, the charging cycle takes only five to twenty seconds, and occurs very infrequently. The SubQ ICD 14 can be programmed to attempt to deliver cardioversion shocks to the heart in timed synchrony with a detected R-wave or without attempting to synchronize the delivery to a detected R-wave. Episode data related to the detection of the tachyarrhythmia and delivery of the CV/DF shock can be stored in RAM for uplink telemetry transmission to an external programmer as is well known in the art to facilitate in diagnosis of the patient's cardiac state. A patient receiving SubQ ICD 14 on a prophylactic basis would be instructed to report each such episode to the attending physician for further evaluation of the patient's condition.

Thus, SubQ ICD 14 monitors the patient's cardiac status and the patient's posture and initiates the immediate delivery of a CV/DF shock through the CV/DF electrodes 113 and 123 in response to detection of a tachycardia requiring CV/DF when the patient is in a substantially upright position. Syncope resulting from the tachycardia can cause serious injury to a patient when they are in a substantially upright position, for example standing or driving a car. Therefore, a programmed shock therapy is not delayed if the patient is determined to be upright at the time of a tachycardia detection. However, if a tachycardia requiring a CV/DF shock is detected and the patient is determined to be in a substantially horizontal position, the shock is delayed. The delay prior to delivering the shock allows the SubQ ICD 14 additional time to attempt ATP therapies and/or verify or discriminate the tachycardia detection as will be described in greater detail below.

SubQ ICD 14 generally includes a telemetry circuit so that it is capable of being programmed by means of external programmer 20 via a 2-way telemetry link 22 (shown in FIG. 1). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Controlling CV/DF shock delivery based on posture sensor feedback, in particular delaying a programmed shock therapy in response to detecting a substantially horizontal position, may be optional ICD functions and may be programmed to be enabled or disabled by a user. Programmers typically communicate with an implanted device via a bidirectional radio-frequency telemetry link, so that the programmer can transmit control commands and operational parameter values to be received by the implanted device, and so that the implanted device can communicate diagnostic and operational data to the programmer. SubQ ICD 14 typically stores detected arrhythmia episode data in a RAM such that episode data, along with any delivered therapy data, are available for transmission to a programmer for review by a clinician. Stored data may be presented in a marker channel format as generally disclosed in U.S. Pat. No. 4,374,382 to Markowitz entitled "Marker Channel Telemetry System for a Medical Device", hereby incorporated herein by reference in its entirety. In one embodiment of the invention, SubQ ICD 14 stores the patient posture detected during a corresponding tachycardia episode. SubQ ICD 14 may generate a marker channel signal indicating detection of a substantially horizontal or upright posture during detection of a tachycardia episode.

Various telemetry systems for providing the necessary communications channels between an external programming unit and an implanted device have been developed and are known in the art. Reference is made, for example, to the following U.S. Patents: U.S. Pat. No. 5,127,404 to Wyborny et al, entitled "Telemetry Format for Implanted Medical Device"; U.S. Pat. No. 4,556,063 to Thompson et al, entitled "Telemetry System for a Medical Device"; and U.S. Pat. No. 6,482,154 to Haubrich et al, entitled "Long range implantable medical device telemetry system with positive patient identification." The Wyborny et al '404, Thompson et al '063, and Haubrich '154 patents are commonly assigned to the assignee of the present invention, and are each hereby incorporated by reference herein in their respective entireties.

Figure 4:
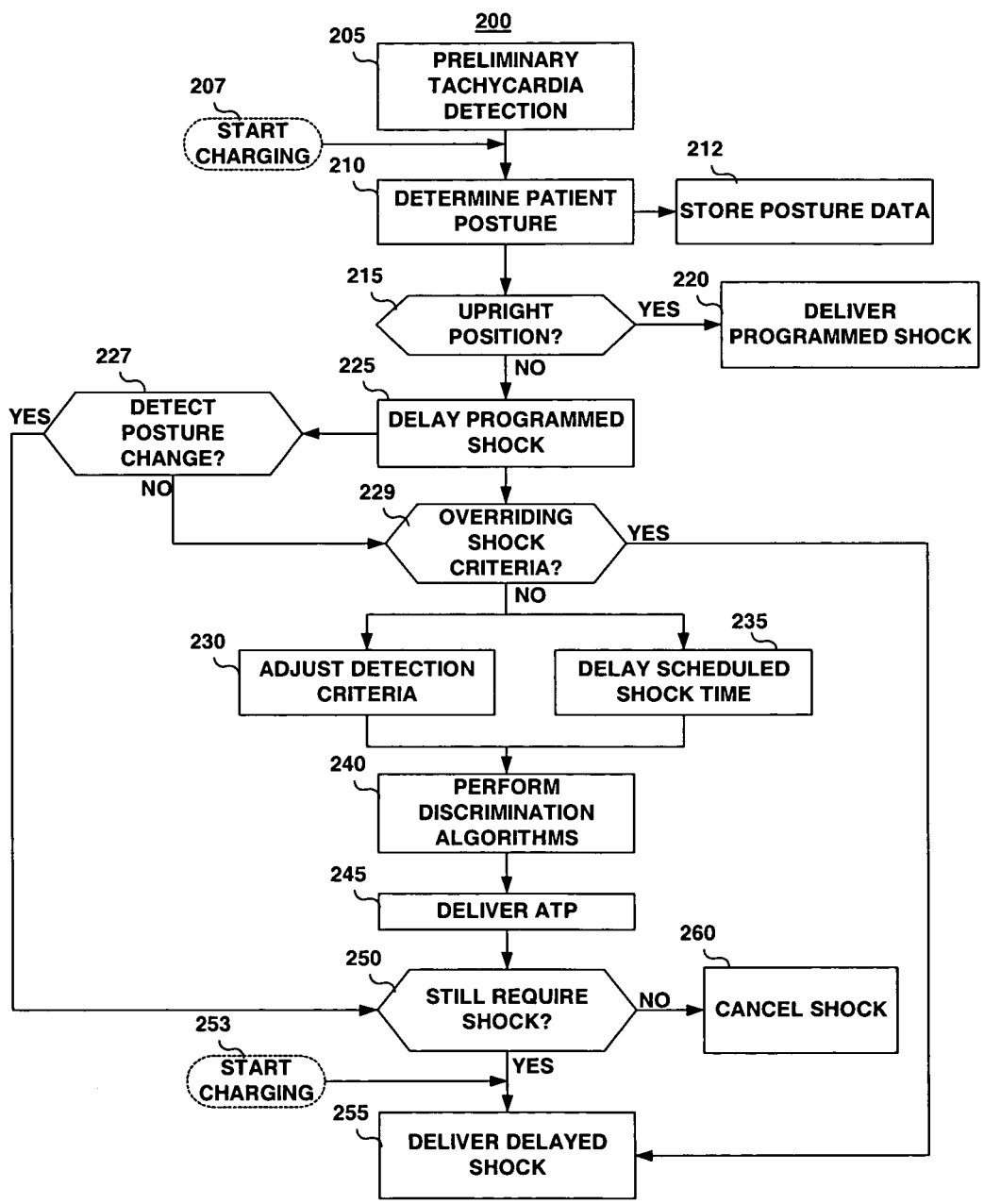
FIG. 4 is a flow chart summarizing one method which may be implemented in an ICD for controlling CV/DF shock delivery based on feedback from a posture sensor.

FIG. 4 is a flow chart summarizing one method which may be implemented in an ICD for controlling CV/DF shock delivery based on feedback from a posture sensor. Flow chart 200 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern ICD, given the disclosure herein, is within the abilities of one of skill in the art.

At block 205, a preliminary tachycardia detection is made based on sensed ECG/EGM signals and any other sensor signals in accordance with a programmed tachycardia detection scheme. Charging of high voltage capacitors may be initiated upon the preliminary detection of the tachycardia as indicated by block 207. At block 210, the patient's posture is determined using a posture sensor signal. As indicated by block 212, the detected posture may be stored, along with tachycardia episode data, to allow transmission of the data to a programmer for display and review by a clinician. If the patient is in a substantially upright position, e.g., standing or sitting, as determined at decision block 215, a cardioversion/defibrillation (CV/DF) shock is delivered according to a programmed menu of therapies. If the patient is determined to be in a substantially horizontal position, e.g. a prone, supine or lateral position, the ICD delays a programmed CV/DF shock at block 225.

Capacitor charging may be initiated at block 207 irrespective of patient position such that, even if a programmed shock is delayed, the capacitors are fully charged, or nearly fully charged, by the end of the delay period. Since a SubQ ICD generally requires longer charge times than an ICD coupled to intracardiac leads, charging may be initiated at block 207 such that capacitor charging occurs during any shock delay period. It is understood that capacitor charging may be initiated later in the shock delay period or even at the end of a shock delay period as long as the total shock delay time and capacitor charging time does not unacceptably delay the delivery of a CV/DF shock. Typically, a CV/DF shock is delivered within the first 10 to 40 seconds after tachycardia detection. If the patient is in a substantially horizontal position, delivery of a CV/DF shock as late as one minute or more after tachycardia detection may be clinically acceptable. The maximum time for which a CV/DF shock may be clinically acceptably delayed will depend on clinical outcomes, individual patient condition and clinician preference.

In some embodiments, the patient position may be monitored throughout a CV/DF shock delay as indicated by block 227. If a change in position is detected, in particular if a change from a non-upright position to a substantially upright position is detected, the shock delay may be terminated prematurely by advancing to block 250 of flowchart 200. At block 250, the device verifies whether a shock is still required, i.e. the device is still detecting tachycardia, and, if so, delivers the delayed shock at block 255. If the device is no longer detecting tachycardia, as determined at block 250, the delayed shock is canceled at block 260.

It is recognized that other physiological data may be collected by the device which may be used to override the decision to delay a shock therapy based on patient position. At block 229, any overriding physiological condition satisfying a shock delivery criterion may prematurely terminate the shock delay and cause delivery of the programmed shock at block 255. Such overriding physiological conditions may relate to blood pressure, blood oxygen saturation, respiration, or any other condition that the device is capable of monitoring.

The CV/DF shock may be delayed by adjusting tachycardia detection criteria as indicated by block 230. Tachycardia detection criteria may be adjusted in a manner that requires additional time for confirming the preliminary tachycardia detection. For example, as described above, the number of tachycardia intervals required to detect may be increased. Alternatively or additionally, a programmed CV/DF shock may be scheduled to be delivered after a predetermined tachycardia episode duration as indicated by block 235.

At block 240, the ICD may optionally execute tachycardia discrimination algorithms during a shock delay to allow accurate diagnosis of the preliminary tachycardia detection. At block 245, the ICD may deliver ATP therapies, if appropriate, during the shock delay in an attempt to terminate the tachycardia and preclude the use of the delayed CV/DF shock. According to one embodiment, the ICD may deliver ATP therapies during capacitor charging as generally described in commonly-assigned U.S. Pat. No. 6,892,094 to Ousdigian et al., incorporated herein by reference in its entirety.

At decision block 250, the ICD determines if the delayed CV/DF shock is still required. During the shock delay, the tachycardia may spontaneously terminate or be successfully terminated by ATP therapies. The preliminary tachycardia detection may be reclassified such that the menu of programmed therapies is changed and no longer includes the delayed CV/DF shock. If the ICD is no longer detecting the originally detected tachycardia, the delayed CV/DF shock is cancelled at block 260. If the ICD is still detecting the tachycardia such that the delayed CV/DF shock is still required, the delayed shock is delivered at block 255. If capacitor charging has not been initiated earlier (prior to or during the shock delay), charging is initiated at block 253 upon determining that a delayed shock is still required. It is understood that if the first shock fails, subsequent shocks may be delivered without delay according to a programmed menu of therapies.

Thus, a method and apparatus for controlling CV/DF shock therapy in response to a posture sensor signal have been presented in the foregoing description with reference to specific embodiments. It is appreciated that various modifications to the referenced embodiments may be made without departing from the scope of the invention as set forth in the following claims.

The invention claimed is:

1. A method for controlling delivery of a therapy for use in an implantable medical device, comprising:
   detecting a tachycardia;
   sensing a signal correlated to a patient's posture;
   determining from the signal if the patient is in a substantially horizontal position;
   delivering a cardioversion/defibrillation shock therapy to the patient using the implantable medical device in response to detecting the tachycardia and to determining that the patient is not in a substantially horizontal position;
   delaying the cardioversion/defibrillation shock therapy delivered using the implantable medical device in response to determining that the patient is in a substantially horizontal position;
   determining from the signal correlated to the patient's posture whether a change in posture has occurred during the delaying of the cardioversion/defibrillation shock therapy; and
   terminating the delaying of cardioversion/defibrillation shock therapy in response to determining that a change in posture has occurred.

2. The method of claim 1 further comprising:
   detecting the tachycardia during the cardioversion/defibrillation shock therapy delay; and
   delivering an anti-tachycardia pacing therapy in response to detecting the tachycardia during the delaying of the cardioversion/defibrillation shock therapy.

3. The method of claim 1 further including comprising:
   detecting the tachycardia during the delaying of the cardioversion/defibrillation shock therapy; and
   performing tachycardia discrimination procedures in response to detecting the tachycardia during the delaying of the cardioversion/defibrillation shock therapy.

4. The method of claim 1, wherein delaying the cardioversion/defibrillation shock therapy comprises adjusting a tachycardia detection criterion.

5. The method of claim 1, wherein delaying the cardioversion/defibrillation shock therapy comprises setting a maximum duration before delivering the cardioversion/defibrillation shock therapy.

6. The method of claim 1 further comprising:
   detecting a termination of the tachycardia during the delaying of the cardioversion/defibrillation shock therapy; and
   canceling the delayed cardioversion/defibrillation shock therapy in response to detecting the tachycardia termination.

7. The method of claim 1 further comprising initiating high voltage capacitor charging during the delaying of the cardioversion/defibrillation shock therapy.

8. The method of claim 1 further comprising:
   determining from the signal if the patient is in a substantially upright position; and adjusting a tachycardia detection criterion in response to determining that the patient is in a substantially upright position to a more aggressive setting than used when the patient is in a substantially horizontal position to more quickly detect a tachycardia when the patient is in a substantially upright position than when the patient is in a substantially horizontal position.

9. The method of claim 1, wherein detecting the tachycardia comprises detecting the tachycardia based on a programmed set of tachycardia detection criteria, wherein delaying the cardioversion/defibrillation shock therapy comprises to adjusting the tachycardia detection criterion.

10. The method of claim 1 further comprising:
determining the patient's posture continuously by monitoring the signal correlated to the patient's posture; and
setting a tachycardia detection criterion according to the determined patient posture.

11. An implantable medical device, comprising:
a first sensor for generating a signal responsive to tachycardia;
an output circuit for generating a cardioversion/defibrillation shock therapy;
an electrode coupled to the output circuit to deliver the cardioversion/defibrillation shock therapy;
a second sensor generating a signal corresponding to a patient position; and
a control circuit for setting a tachycardia detection criterion, the control circuit coupled to the first sensor, the second sensor, and the output circuit, wherein the control circuit is configured to:
detect a tachycardia using the tachycardia detection criterion and the signal responsive to tachycardia from the first sensor,
determine the patient position using the signal corresponding to the patient position from the second sensor,
initiate the delivery of the cardioversion/defibrillation shock therapy to the patient using the electrode and output circuit in response to detecting the tachycardia and determining that the patient is not in a substantially horizontal position,
delay the delivery of the cardioversion/defibrillation shock therapy in response to determining the patient is in a substantially horizontal position,
determine whether a change in posture has occurred using the signal corresponding to the patient position from the second sensor during to the delaying of the delivery of the cardioversion/defibrillation shock therapy, and
terminate the delaying of the delivery of cardioversion/defibrillation shock therapy in response to determining that a change in posture has occurred.

12. The device of claim 11 further comprising a low-voltage output circuit coupled to the control circuit and configured to deliver an anti-tachycardia pacing therapy wherein the control circuit is further configured to initiate the delivery of the anti-tachycardia pacing therapy using the low-voltage output circuit in response to detecting the tachycardia during the delaying of the delivery of the cardioversion/defibrillation shock therapy.

13. The device of claim 11 further comprising a processor coupled to the control circuit and configured to cooperate with the control circuit to discriminate the detected tachycardia during the delaying of the delivery of the cardioversion/defibrillation shock therapy.

14. The device of claim 11, wherein the control circuit delays the cardioversion/defibrillation shock therapy by adjusting a tachycardia detection criterion.

15. The device of claim 11, wherein the control circuit delays the cardioversion/defibrillation shock therapy by setting a maximum duration before delivering the cardioversion/defibrillation shock therapy.

16. The device of claim 11, wherein the output circuit comprises a high voltage capacitor, and wherein the control circuit is further configured to initiate charging of the high voltage capacitor during the delaying of the delivery of the cardioversion/defibrillation shock therapy.

17. A computer readable medium storing a set of instructions, which when implemented in an implantable medical device causes the device to perform a method, the method comprising:
detecting a tachycardia,
sensing a signal correlated to a patient's posture;
determining from the signal if the patient is in a substantially horizontal position;
delivering a cardioversion/defibrillation shock therapy to the patient using the implantable medical device in response to detecting the tachycardia and determining that the patient is not in a substantially horizontal position;
delaying the cardioversion/defibrillation shock therapy delivered using the implantable medical device in response to determining the patient is in a substantially horizontal position, wherein delaying the cardioversion/defibrillation shock therapy comprises adjusting a tachycardia detection criterion used by the medical device to determine when the cardioversion/defibrillation shock therapy is needed in response to a tachycardia detection;
determining from the signal correlated to the patient's posture whether a change in posture has occurred during the delaying of the cardioversion/defibrillation shock therapy; and
terminating the delaying of the cardioversion/defibrillation shock therapy in response to determining that a change in posture has occurred.

18. The computer readable medium of claim 17, the method further comprising:
detecting the tachycardia during the delaying of the cardioversion/defibrillation shock therapy; and
delivering an anti-tachycardia pacing therapy in response to detecting the tachycardia during the delaying of the cardioversion/defibrillation shock therapy.

19. The computer readable medium of claim 17, the method further comprising:
detecting the tachycardia during the delaying of the cardioversion/defibrillation shock therapy; and
discriminating the detected tachycardia in response to detecting the tachycardia during the delaying of the cardioversion/defibrillation shock therapy.

20. The computer readable medium of claim 17, wherein adjusting the tachycardia detection criterion comprises adjusting a number of tachycardia intervals required to detect the tachycardia.

21. The computer readable medium of claim 17, wherein delaying the cardioversion/defibrillation shock therapy further comprises setting a maximum duration before delivering the cardioversion/defibrillation shock therapy.

* * * * *

UNITED STATES PATENT AND TRADEMARK OFFICE
CERTIFICATE OF CORRECTION

PATENT NO. : 8,478,399 B2
APPLICATION NO. : 11/343346
DATED : July 2, 2013
INVENTOR(S) : Paul DeGroot et al.

Page 1 of 1

It is certified that error appears in the above-identified patent and that said Letters Patent is hereby corrected as shown below:

In the Claims

Col. 12, line 42, delete the word "including".

Signed and Sealed this
Third Day of September, 2013

Teresa Stanek Rea
*Acting Director of the United States Patent and Trademark Office*